(12) United States Patent  (10) Patent No.: US 7,740,478 B2
Hörth et al.  (45) Date of Patent: Jun. 22, 2010

(54) APPLICATOR FOR DENTAL COMPOUNDS

(75) Inventors: Hans Hörth, Hamburg (DE); Karsten Lamott, Hamburg (DE); Edgar Lein, Schenefeld (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 1261 days.

(21) Appl. No.: 11/231,567

(22) Filed: Sep. 21, 2005

(65) Prior Publication Data

US 2006/0178640 A1  Aug. 10, 2006

(51) Int. Cl.
 *A61C 5/04* (2006.01)
(52) U.S. Cl. ........................................ 433/90
(58) Field of Classification Search ............... 433/80, 433/81, 82, 84, 88, 89–90; 601/162–165; 604/19, 310–311; 222/386–391, 326–327
See application file for complete search history.

(56) References Cited

U.S. PATENT DOCUMENTS

| | | | | |
|---|---|---|---|---|
| 4,997,371 A | * | 3/1991 | Fischer | 433/90 |
| 5,626,473 A | * | 5/1997 | Muhlbauer et al. | 433/89 |
| 5,782,633 A | * | 7/1998 | Muhlbauer | 433/90 |
| 6,161,734 A | * | 12/2000 | Winkler | 222/390 |
| 6,585,511 B2 | * | 7/2003 | Dragan et al. | 433/90 |
| 6,790,037 B1 | * | 9/2004 | Orecchia | 433/90 |

* cited by examiner

*Primary Examiner*—Cris L Rodriguez
*Assistant Examiner*—Matthew M Nelson
(74) *Attorney, Agent, or Firm*—Alix, Yale & Ristas, LLP

(57) ABSTRACT

An applicator for dental compounds includes a shaft, the front end of which can be connected with the aid of a fastening device to a syringe containing the dental compound, and a plunger. The shaft contains a ram for advancing the plunger. The fastening device has an inner sleeve, attached to the shaft, and an outer sleeve, attached on the inner sleeve rotatably with respect to it. The inner sleeve is substantially cylindrical and has such a cavity that its cross section is substantially U-shaped. Clamping takes place as a result of eccentricity.

13 Claims, 5 Drawing Sheets

APPLICATOR FOR DENTAL COMPOUNDS

CROSS-REFERENCE TO RELATED APPLICATIONS

This application claims priority under 35 U.S.C. §119 from DE 10 2004 046 417.0, filed Sep. 24, 2004.

BACKGROUND OF THE INVENTION

This invention relates generally to applicators for dental compounds. More particularly, the present invention relates to applicators for dental compounds having a shaft, the front end of which can be connected with the aid of a fastening device to a syringe containing the dental compound and a plunger and which shaft contains a ram for advancing the plunger.

There are various applicators designed for receiving a fastened-on syringe, the dental compound contained in which can be expelled with the aid of a ram. The fastening devices concerned have various disadvantages. Some are difficult to operate or complicated, with others it is not ensured that the syringe is really held reliably.

In the case of an applicator of the type stated at the beginning (EP 0 714 638 A1), the syringe is inserted from the side into an undercut opening of the shaft. Although the syringe is prevented from falling out as soon as the ram has been advanced far enough, reaching into the syringe, the syringe can fall out before that.

In the case of a further already known applicator, although the syringe is prevented from falling out by an external rotatable sleeve (U.S. Pat. No. 6,790,037 B1), the syringe is not reliably held, since it can turn in the holder, which presents problems in particular if the discharge ends are angled away.

SUMMARY OF THE INVENTION

The object of the invention is to provide an applicator with which the syringe is securely held by simple means even before the ram penetrates into it.

In the case of an applicator for dental compounds with a shaft, the front end of which can be connected with the aid of a fastening device to a syringe containing the dental compound and a plunger and which shaft contains a ram for advancing the plunger, the fastening device having an inner sleeve, attached to the shaft, and an outer sleeve, attached on said inner sleeve rotatably with respect to it, the inner sleeve being substantially cylindrical and having such a cavity extending in the longitudinal direction that its cross section is substantially U-shaped, the solution achieving the object as provided by the invention consists in that the outer sleeve has an inwardly directed, substantially wedge-shaped projection, which protrudes into the cavity and, as a result of eccentricity, exerts a clamping force on the syringe when the outer sleeve is turned from the insertion position for the syringe into the holding position.

Before the insertion of the syringe, the outer sleeve is turned in such a way that the cavity of the inner sleeve is exposed. The syringe can then be inserted from the side. By turning the outer sleeve, the cavity can be at least partially closed by the wedge-shaped projection, so that the syringe can no longer fall out. As a result of the eccentricity, a clamping force is thereby produced, with the effect of securing the syringe against twisting, which is important when the cannula-like discharge end of the syringe is angled away.

In the case of one embodiment, this eccentricity is brought about by providing that, although both sleeves are concentric, the inner sleeve has an inwardly directed elevation in the form of a point or ridge, which cuts into the circumference of the syringe. As a result, the syringe is held eccentrically and clamped by the wedge-shaped projection, which moves concentrically in relation to the inner sleeve, when the outer sleeve is turned.

In this case, the material of the elevation of the inner sleeve is expediently harder than the material of the syringe. In the case of another embodiment, the entire material of the inner sleeve is harder than the material of the syringe in the region of the fastening device.

Another advantageous embodiment is distinguished by the fact that the cylindrical outer surface of the inner sleeve is eccentric in relation to the inner surface of the sleeve. In this way, the outer sleeve, and with it the wedge-shaped projection, is moved eccentrically in relation to the inner surface of the sleeve and the outer surface of the syringe when the sleeve is turned, in order in this way to achieve the desired clamping effect.

If the shaft is provided with a device for advancing the ram, the applicator can be held by the dentist like a pencil or brush, a pistol-shaped actuating device then not being required. Such a device for advancing the ram is known (EP 0 714 638 A1). It expediently has a gear wheel for advancing the ram, which engages in a toothed rack provided on the ram.

A further advantageous embodiment is distinguished by the fact that the syringe is provided with an application aid at the discharge end. Particularly advantageous in this case as application aids are a brush, a sponge or a similar element with which a low-viscosity dental compound, for example caustic agents, adhesion promoters, sealing or fluoridating varnishes, can be applied to the teeth or the gums.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

Figure 1:
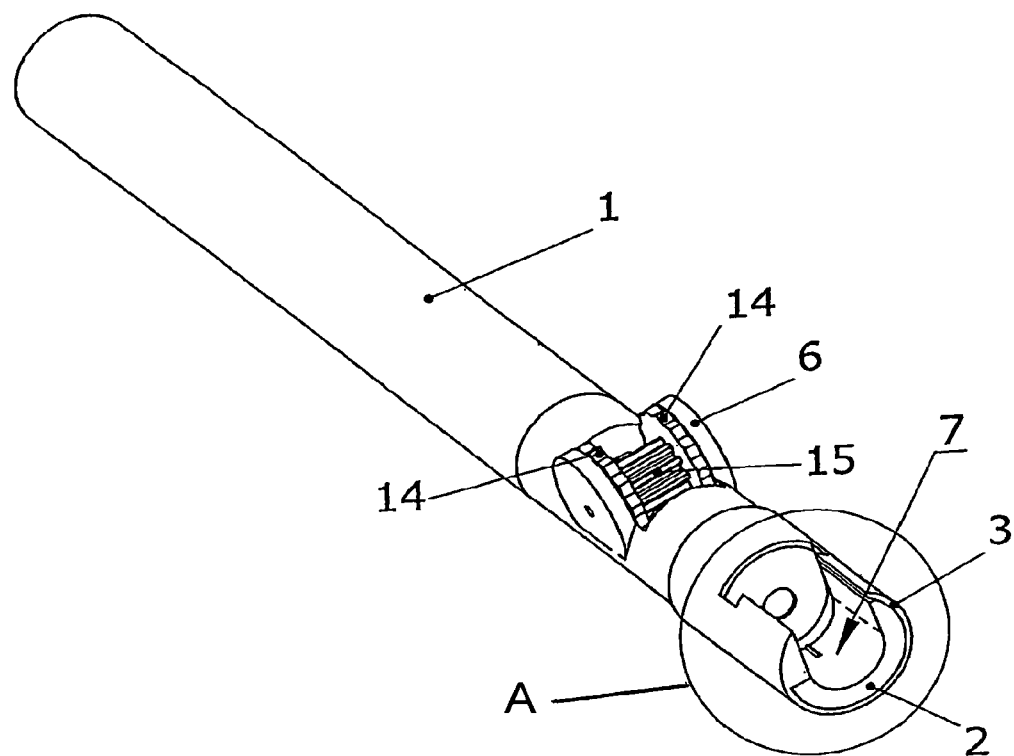
FIG. 1 is a first embodiment of an applicator in accordance with the invention.
Figure 2:
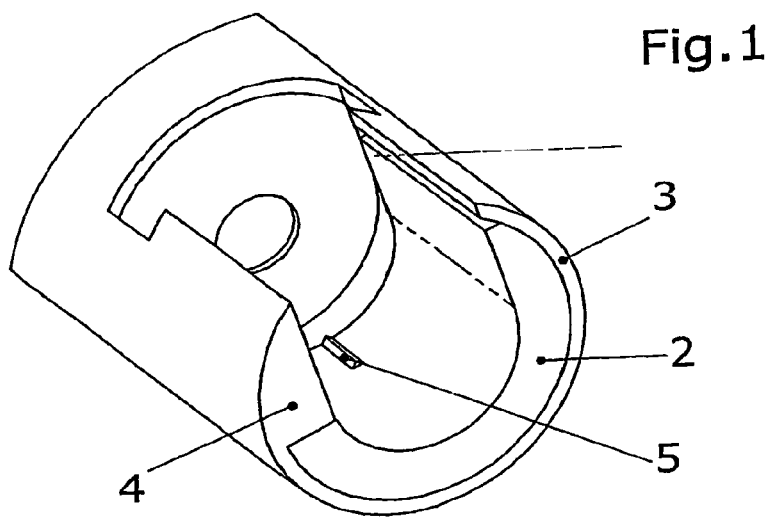
FIG. 2 is an enlarged view of Section A of FIG. 1.

Reference is made firstly to FIGS. 1 and 2. The embodiment shown there of the applicator according to the invention has a shaft 1, to which an inner sleeve 2 is fastened. This inner sleeve is surrounded by an outer sleeve 3, arranged rotatably with respect to said inner sleeve. Both sleeves 2, 3 have cavities 7, extending in the longitudinal direction. The outer sleeve 3 has a wedge-shaped inwardly directed projection 4, which in the position shown in FIG. 3b exposes the cavity 7 of the inner sleeve 2 for the insertion of the syringe 8. A ridge-shaped projection 5 is provided in the interior of the inner sleeve 2. Shown by 6 is an actuating device with which the ram (not shown in FIGS. 1 and 2) can be advanced.

Figure 3A:
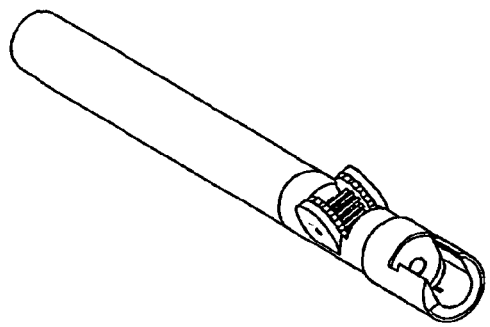
FIGS. 3a and 3b are perspective and front views, respectively, showing the applicator of FIG. 1, with the outer sleeve in the insertion position.
Figure 3B:
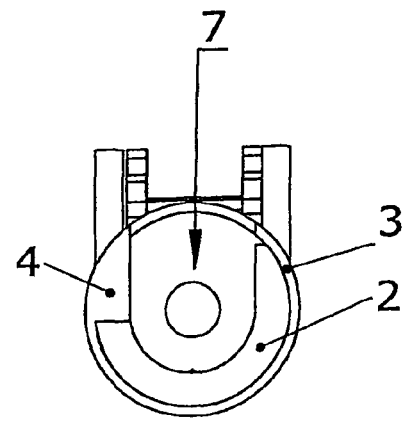
Figure 4A:
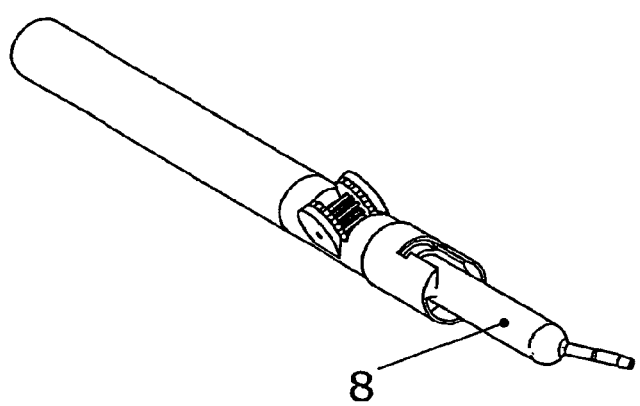
FIGS. 4a and 4b are perspective and front views, respectively, showing a syringe installed in the applicator of FIG. 1, with the outer sleeve rotated between the insertion position and the holding position.
Figure 4B:
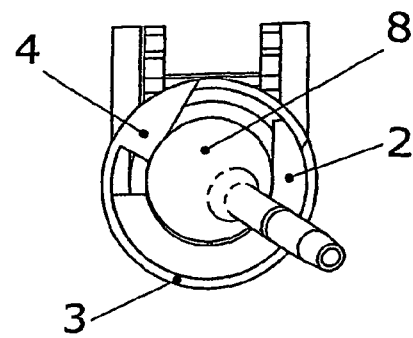
Figure 5A:
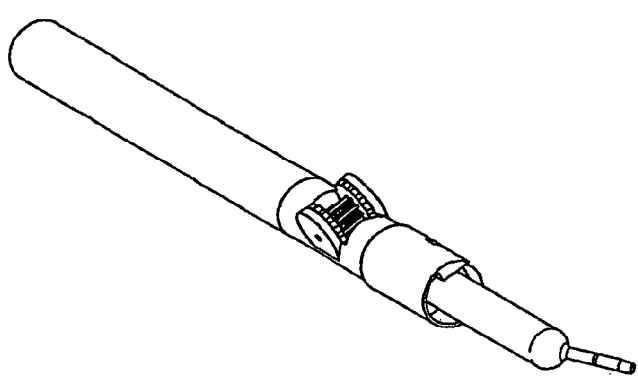
FIGS. 5a and 5b are perspective and front views, respectively, showing a syringe installed in the applicator of FIG. 1, with the outer sleeve in the holding position.
Figure 5B:
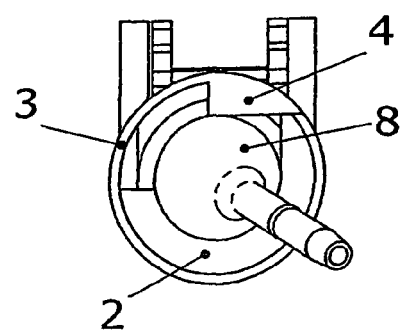

In FIGS. 3a and 3b, the applicator is shown in the position that is also shown in FIG. 1, that is to say before the insertion of the syringe 8. The syringe can be inserted from above into the substantially U-shaped cavity 7 of the inner sleeve 2 and of the outer sleeve 3. In FIGS. 4a and 4b it is shown how the syringe 8 is inserted and the outer sleeve 3 has already been turned a little clockwise, in order to enclose the syringe 8. The wedge-shaped projection 4 thereby slides over the syringe 8 or a corresponding flange 9 of the syringe 8, which is shown for example in FIG. 6. Since the syringe 8 is eccentrically mounted as a result of the ridge-like projection 5 (FIG. 2), the wedge-shaped projection 4 exerts a compressive force on the flange 9 of the syringe 8 and, as a result, secures the latter against twisting. The ridge-like projection 5 thereby cuts into the flange 9, in order to prevent twisting in this way. Shown in FIGS. 5a and 5b is the situation after the outer sleeve 3 has been turned as far as the stop of the wedge-shaped element 4, in order in this way to secure the syringe 8 reliably. As a result, the syringe is secured against twisting, so that the dentist can accurately set the alignment of the cannula-like discharge end 10 of the syringe.

Figure 6:
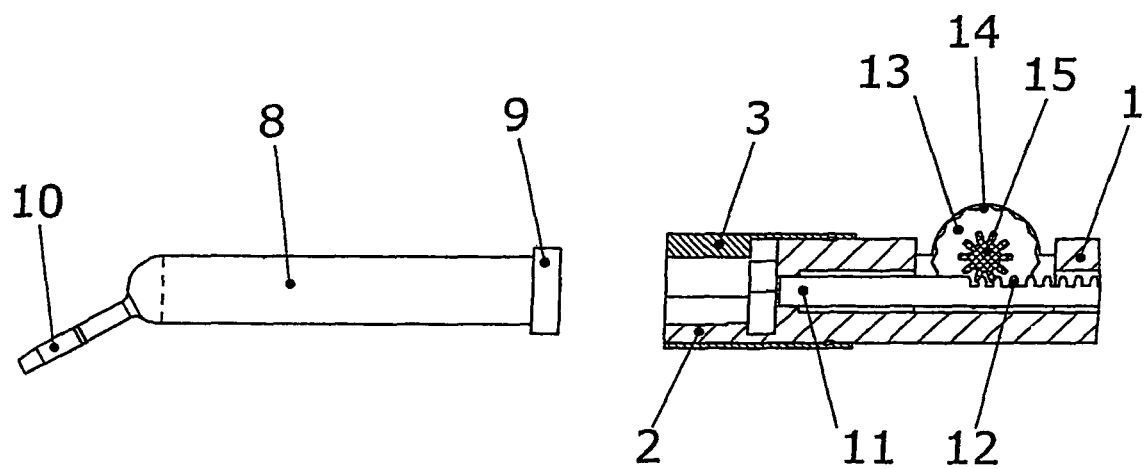
FIG. 6 is a side view, partly in cross-section of the applicator of FIG. 1 and a syringe.

The details of the advancing device 6 are shown in FIG. 6. Provided in the shaft 1 is the ram 11, which is provided with a toothed rack 12. An actuating wheel 13 with two grooved surfaces 14 encloses a smaller gear wheel 15 (see also FIG. 1), which interacts with the toothed rack 12. Since the circumference of the grooved surfaces 14 is greater than that of the gear wheel 15, a reduction in the gearing is obtained in this way, so that the movement of the ram 11, and with it the expulsion of the dental compound, can be regulated particularly sensitively.

Figure 7:
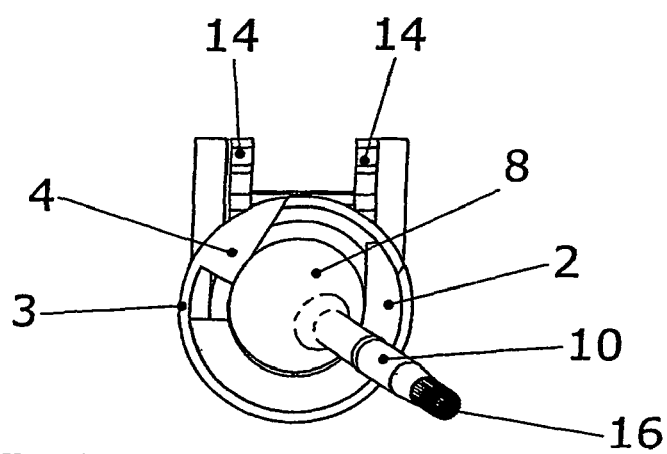
FIG. 7 is a front view of the applicator of FIG. 1 and a syringe having a brush application aid.
Figure 8:
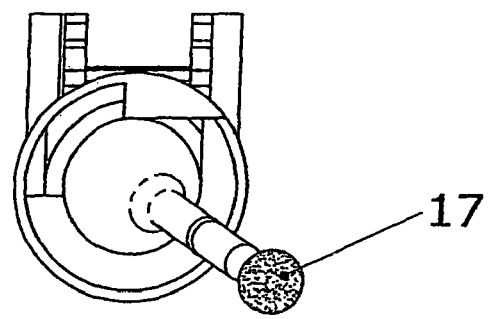
FIG. 8 is a front view of the applicator of FIG. 1 and a syringe having a sponge application aid.

In FIGS. 7 and 8 it is shown that the cannula-like discharge ends are provided with application aids. In the case of FIG. 7, this is a brush 16, in the case of FIG. 8 it is a sponge 17. The application of liquids is facilitated by these application aids. The dentist does not have to keep dipping the corresponding application aid into a supply of liquid.

Figure 9:
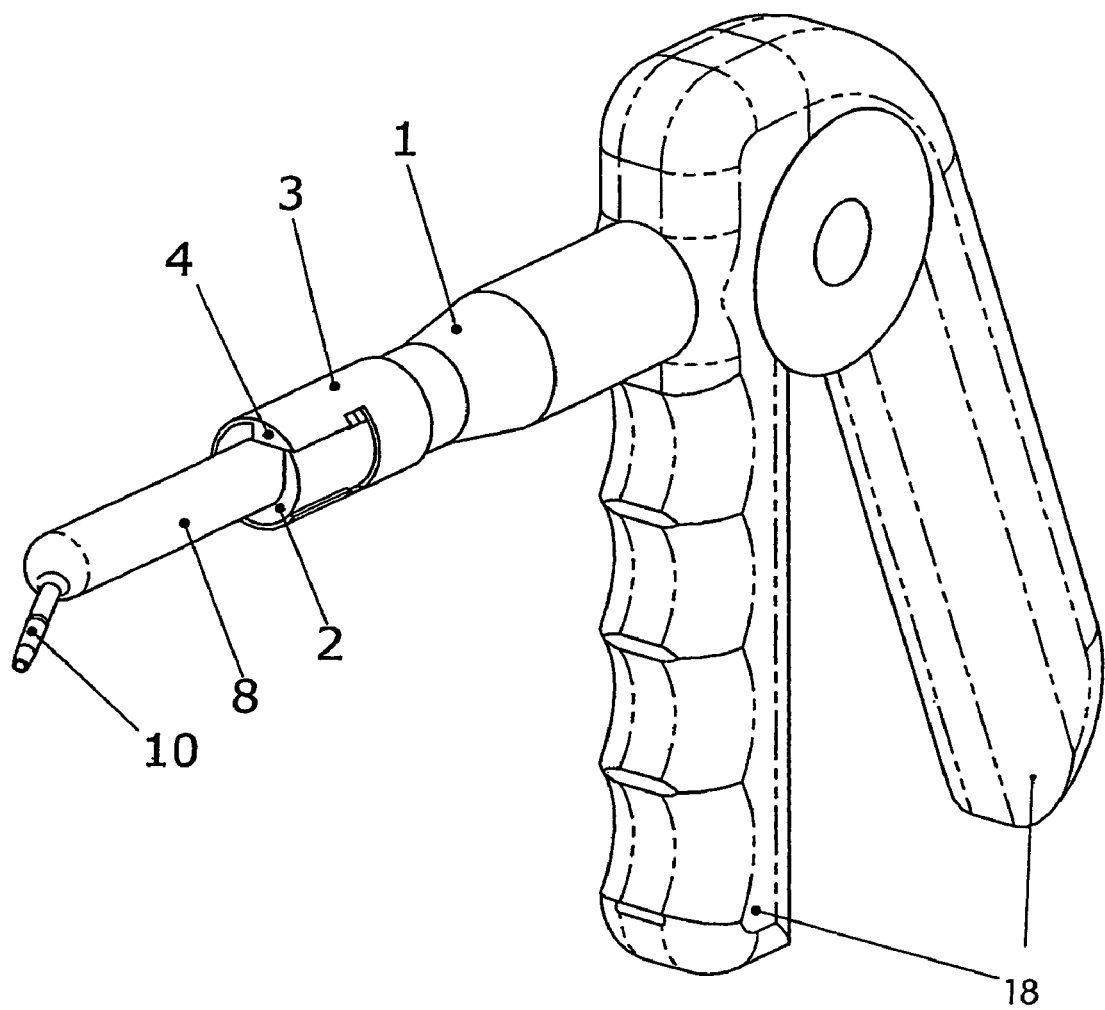
FIG. 9 is a perspective view of a second embodiment of an applicator in accordance with the invention.

In the case of the embodiment of FIG. 9, the applicator is formed like a pistol, so that the actuation of the syringe no longer takes place by means of the wheel 13 but by pressing together the two hand-held grips 18.

Figure 11:
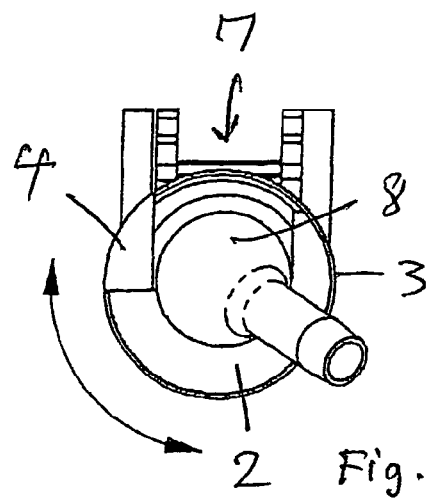
FIG. 11 is a front view showing a syringe installed in the applicator of FIG. 10, with the outer sleeve in the insertion position.
Figure 12:
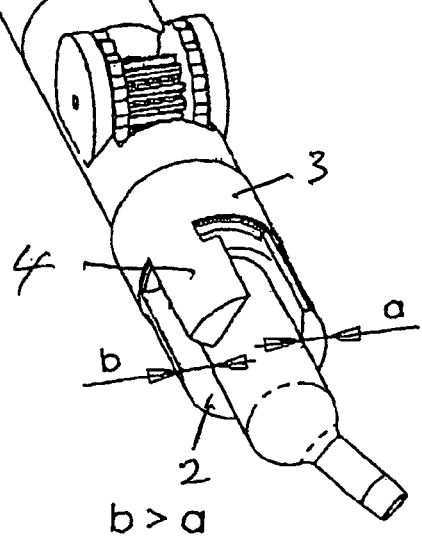
FIG. 12 is a front view showing a syringe installed in the applicator of FIG. 10, with the outer sleeve in the holding position.
Figure 10:
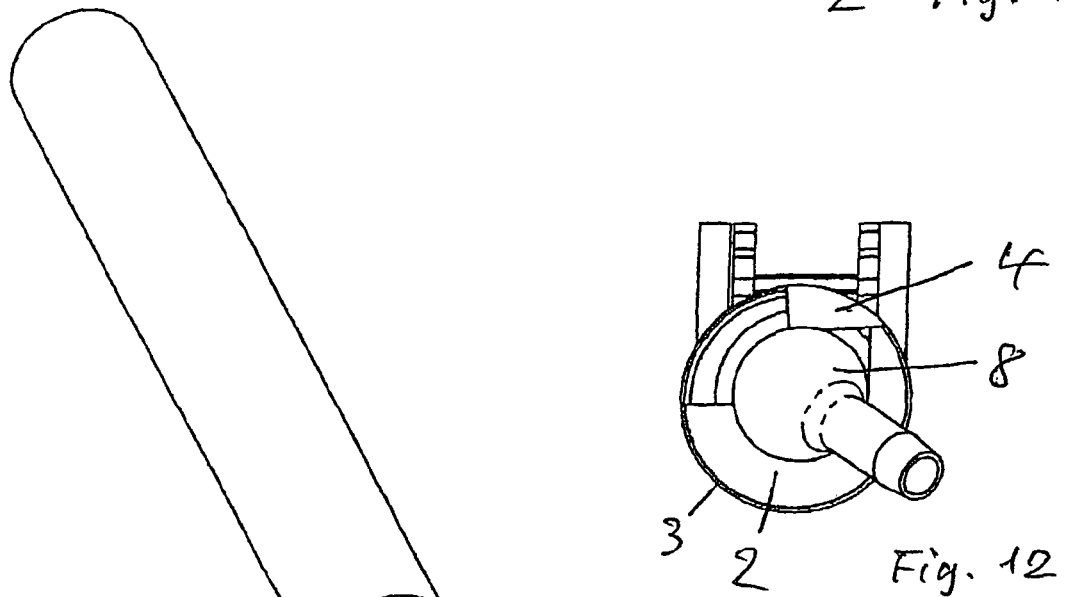
FIG. 10 is a perspective view of a third embodiment of an applicator in accordance with the invention.

In the case of the embodiment of FIG. 10 to FIG. 12, the outer surface of the inner sleeve 2 is eccentric in relation to the inner surface of the same. As is shown in FIG. 10, the wall thickness b of the inner sleeve 2 on the side on the left in FIG. 10 is greater than the wall thickness a on the side on the right. If the outer sleeve 3 with the wedge-shaped projection 4 is turned, the wedge-shaped projection 4 moves eccentrically in relation to the inner surface of the inner sleeve 2, and consequently eccentrically in relation to the outer surface of the syringe 8. Although the syringe 8 is also concentrically arranged in relation to the ram 11, an eccentric clamping effect is achieved in this way. FIG. 11 shows the applicator after insertion of the syringe 8, the wedge-shaped projection 4 still exposing the cavity 7 of the inner sleeve 2. In the position shown in FIG. 12, the outer sleeve 3 with the wedge-shaped projection 4 has been turned around the outer surface of the outer sleeve 2, so that the wedge-shaped projection 4 clamps the syringe 8.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An applicator for a syringe containing a dental compound and having a plunger for expelling the dental compound from the syringe, the applicator comprising:
   a shaft having a front end;
   a ram extending longitudinally within the shaft, the ram being adapted for advancing the plunger to expel the dental compound from the syringe; and
   a fastening device disposed at the front end of the shaft, the fastening device including
      an inner sleeve attached to the shaft, the inner sleeve being substantially cylindrical and defining a longitudinally extending cavity, the inner sleeve having a substantially U-shaped cross-section, and
      an outer sleeve rotatably attached to the inner sleeve, the outer sleeve having a substantially wedge-shaped projection extending into the cavity of the inner sleeve, the outer sleeve being rotatably movable between an insertion position and a holding position;
   wherein the cavity of the inner sleeve is adapted for eccentrically receiving the syringe when the outer sleeve is in the insertion position and the outer sleeve projection is adapted to exert a clamping force on the syringe when the outer sleeve is rotated to the holding position.

2. The applicator as claimed in claim 1, wherein the inner sleeve has inner and outer surfaces, the outer surface being substantially cylindrical and eccentric in relation to the inner surface.

3. The applicator as claimed in claim 1, wherein the shaft includes a ram advancement device.

4. The applicator as claimed in claim 3, wherein the ram advancement device includes a gear wheel, which engages a toothed rack on the ram.

5. A system for applying a dental compound comprising:
   a syringe adapted to house the dental compound, the syringe including a plunger adapted to expel the dental compound from the syringe; and
   an applicator including
      a shaft having a front end;
      a ram extending longitudinally within the shaft, the ram advancing the plunger to expel the dental compound from the syringe; and
      a fastening device disposed at the front end of the shaft, the fastening device including
         an inner sleeve attached to the shaft, the inner sleeve being substantially cylindrical and defining a longitudinally extending cavity, the inner sleeve having a substantially U-shaped cross-section, and
         an outer sleeve rotatably attached to the inner sleeve, the outer sleeve having a substantially wedge-shaped projection extending into the cavity of the inner sleeve, the outer sleeve being rotatably movable between an insertion position and a holding position;

wherein the cavity of the inner sleeve eccentrically receives the syringe when the outer sleeve is in the insertion position and the outer sleeve projection exerts a clamping force on the syringe when the outer sleeve is rotated to the holding position.

6. The system as claimed in claim 5, wherein both sleeves are concentric and the inner sleeve has an inwardly extending elevation which cuts into a circumference of the syringe.

7. The system as claimed in claim 6, wherein the elevation of the inner sleeve and the syringe are each composed of a material, the material of the elevation of the inner sleeve being harder than the material of the syringe in a region of the fastening device.

8. The system as claimed in claim 6, wherein the elevation has the form of a point or ridge.

9. The system as claimed in claim 5, wherein the syringe also has an axis and a cannula-like discharge end that is angled away from the syringe axis.

10. The system as claimed in claim 5, wherein the inner sleeve and the syringe are each composed of a material, the material of the inner sleeve being harder than the material of the syringe in a region of the fastening device.

11. The system as claimed in claim 5, wherein the syringe also has an application aid disposed at a discharge end.

12. The system as claimed in claim 11, wherein the application aid is a brush.

13. The system as claimed in claim 11, wherein the application aid is a sponge.

* * * * *